United States Patent
Zipprich et al.

(10) Patent No.: US 9,687,321 B2
(45) Date of Patent: Jun. 27, 2017

(54) DENTAL IMPLANT SYSTEM

(75) Inventors: Holger Zipprich, Malchen (DE);
Huang Mao Sung, Taichung (TW)

(73) Assignee: BIODENTA SWISS AG, Switzerland (CH)

( * ) Notice: Subject to any disclaimer, the term of this patent is extended or adjusted under 35 U.S.C. 154(b) by 17 days.

(21) Appl. No.: 14/003,917

(22) PCT Filed: Mar. 20, 2012

(86) PCT No.: PCT/EP2012/001220
§ 371 (c)(1),
(2), (4) Date: Nov. 22, 2013

(87) PCT Pub. No.: WO2012/126609
PCT Pub. Date: Sep. 27, 2012

(65) Prior Publication Data
US 2014/0134570 A1    May 15, 2014

(30) Foreign Application Priority Data
Mar. 21, 2011    (EP) .................................. 11002296

(51) Int. Cl.
*A61C 8/00*    (2006.01)
(52) U.S. Cl.
CPC .............. *A61C 8/006* (2013.01); *A61C 8/005* (2013.01); *A61C 8/0069* (2013.01)
(58) Field of Classification Search
CPC ....... A61C 8/005; A61C 8/006; A61C 8/0066; A61C 8/0069
(Continued)

(56) References Cited

U.S. PATENT DOCUMENTS

| 4,270,905 A | 6/1981 | Mohammed |
| 4,324,550 A | 4/1982 | Reuther et al. |

(Continued)

FOREIGN PATENT DOCUMENTS

| CH | 642838 | 5/1984 |
| CH | 696625 | 8/2007 |

(Continued)

OTHER PUBLICATIONS

International Search Report prepared by the European Patent Office on Jul. 30, 2012, for International Application No. PCT/EP2012/001220.

(Continued)

*Primary Examiner* — Cris L Rodriguez
*Assistant Examiner* — Hao D Mai
(74) *Attorney, Agent, or Firm* — Steven Reiss

(57) ABSTRACT

A dental-implant having a first implant part provided for being inserted into a jawbone and having a second implant part associated therewith, provided for fixing a dental prosthetic piece, the implant parts being mechanically connectable to each other via a connection pin which is formed onto one of the implant parts and which can be pushed into a receiving channel provided in the other implant part, and the outer cross-section of the connection pin and, matching said cross-section, the inner cross-section of the receiving channel associated therewith, each being designed in an indexing area as a polygon, shall enable a particularly simple mounting. For this purpose, the connection pin has at least two sections in the indexing area, the outer edges of the polygon being rounded more strongly in a first, end-side section than in a second section.

16 Claims, 3 Drawing Sheets

(58) Field of Classification Search
USPC .................................. 433/173–176, 201.1
See application file for complete search history.

(56) References Cited

U.S. PATENT DOCUMENTS

| | | | |
|---|---|---|---|
| 4,731,085 A | 3/1988 | Koch | |
| 4,793,808 A | 12/1988 | Kirsch | |
| 4,832,601 A | 5/1989 | Linden | |
| 4,850,870 A | 7/1989 | Lazzara et al. | |
| 4,854,872 A | 8/1989 | Detsch | |
| 4,876,148 A | 10/1989 | Virkar et al. | |
| 5,015,186 A | 5/1991 | Detsch | |
| 5,125,971 A | 6/1992 | Nonami et al. | |
| 5,135,395 A | 8/1992 | Marlin | |
| 5,195,892 A * | 3/1993 | Gersberg | 433/174 |
| 5,246,370 A | 9/1993 | Coatman | |
| 5,281,140 A | 1/1994 | Niznick | |
| 5,302,126 A | 4/1994 | Wimmer et al. | |
| 5,336,465 A | 8/1994 | Matsunaga et al. | |
| 5,407,359 A | 4/1995 | Balfour et al. | |
| 5,425,639 A | 6/1995 | Anders et al. | |
| 5,437,551 A | 8/1995 | Chalifoux | |
| 5,553,983 A * | 9/1996 | Shinjo | 411/404 |
| 5,674,072 A | 10/1997 | Moser et al. | |
| 5,766,179 A | 6/1998 | Faccioli et al. | |
| 5,782,918 A * | 7/1998 | Klardie et al. | 606/60 |
| 5,785,525 A | 7/1998 | Weissman | |
| 5,947,733 A | 9/1999 | Sutter et al. | |
| 5,954,505 A | 9/1999 | Ford | |
| 5,984,680 A * | 11/1999 | Rogers | 433/173 |
| 5,989,026 A | 11/1999 | Rogers et al. | |
| 6,158,310 A * | 12/2000 | Goss et al. | 81/121.1 |
| 6,217,331 B1 | 4/2001 | Rogers et al. | |
| 6,419,489 B1 * | 7/2002 | Jorneus et al. | 433/141 |
| 6,500,003 B2 | 12/2002 | Nichinonni | |
| 6,537,069 B1 | 3/2003 | Simmons, Jr. | |
| 6,575,057 B1 * | 6/2003 | Ploeger | 81/53.2 |
| 6,652,765 B1 | 11/2003 | Beaty | |
| 7,104,797 B2 * | 9/2006 | Rassoli | 433/173 |
| 7,144,622 B1 | 12/2006 | Stecher et al. | |
| 7,225,710 B2 * | 6/2007 | Pacheco, Jr. | 81/460 |
| 7,249,949 B2 * | 7/2007 | Carter | 433/173 |
| 7,309,231 B2 * | 12/2007 | Engman | 433/173 |
| 8,038,442 B2 * | 10/2011 | Hurson | 433/173 |
| 8,123,524 B2 * | 2/2012 | Anitua Aldecoa | 433/173 |
| 8,291,795 B2 * | 10/2012 | Hughes et al. | 81/460 |
| 8,347,761 B2 * | 1/2013 | Goss | 81/121.1 |
| 8,408,904 B2 * | 4/2013 | Purga et al. | 433/173 |
| 8,632,336 B2 * | 1/2014 | Rossler et al. | 433/174 |
| 8,932,663 B2 | 1/2015 | Ritz et al. | |
| 2002/0177105 A1 * | 11/2002 | Engman | 433/173 |
| 2003/0013068 A1 | 1/2003 | Gittleman | |
| 2003/0194679 A1 | 10/2003 | Odrich et al. | |
| 2003/0232309 A1 | 12/2003 | Dinkelacker et al. | |
| 2004/0121285 A1 | 6/2004 | Wu | |
| 2004/0185417 A1 | 9/2004 | Rassoli | |
| 2004/0185419 A1 | 9/2004 | Schulter et al. | |
| 2005/0042573 A1 | 2/2005 | Lustig et al. | |
| 2005/0166724 A1 * | 8/2005 | Castaneda | 81/436 |
| 2005/0186537 A1 | 8/2005 | Gersberg | |
| 2006/0110706 A1 | 5/2006 | Jorneus et al. | |
| 2006/0141418 A1 | 6/2006 | Heo | |
| 2006/0172257 A1 | 8/2006 | Niznick | |
| 2007/0037121 A1 * | 2/2007 | Carter | 433/173 |
| 2008/0182227 A1 | 7/2008 | Wolf et al. | |
| 2008/0241789 A1 | 10/2008 | Mundorf | |
| 2008/0261178 A1 | 10/2008 | Homann et al. | |
| 2008/0293015 A1 | 11/2008 | Wong et al. | |
| 2009/0075236 A1 | 3/2009 | Towse et al. | |
| 2009/0123889 A1 | 5/2009 | Mehrhof | |
| 2009/0123890 A1 | 5/2009 | Purga et al. | |
| 2009/0123891 A1 | 5/2009 | Rosenberg et al. | |
| 2009/0239195 A1 | 9/2009 | Wohrle et al. | |
| 2009/0305190 A1 | 12/2009 | Zipprich | |
| 2010/0099058 A1 | 4/2010 | Wang et al. | |
| 2010/0178636 A1 | 7/2010 | Stephan et al. | |
| 2010/0196851 A1 | 8/2010 | Konig | |
| 2010/0196852 A1 | 8/2010 | Baruc et al. | |
| 2010/0240009 A1 | 9/2010 | Gogarnoiu | |
| 2010/0304334 A1 | 12/2010 | Layton | |
| 2011/0065064 A1 | 3/2011 | Kahdemann et al. | |
| 2011/0123951 A1 | 5/2011 | Lomicka et al. | |
| 2011/0212417 A1 | 9/2011 | Beekmans et al. | |
| 2011/0223562 A1 | 9/2011 | Zipprich | |
| 2012/0288824 A1 | 11/2012 | Nordin et al. | |
| 2013/0108984 A1 | 5/2013 | Zipprich | |
| 2013/0337410 A1 | 12/2013 | Ten Bruggenkate | |
| 2014/0106305 A1 | 4/2014 | Jacoby et al. | |
| 2014/0212844 A1 | 7/2014 | Zipprich | |
| 2015/0037759 A1 | 2/2015 | Zipprich | |
| 2015/0157427 A1 | 6/2015 | Purga et al. | |

FOREIGN PATENT DOCUMENTS

| | | |
|---|---|---|
| CN | 2216818 | 1/1996 |
| CN | 1889896 | 1/2007 |
| CN | 101146491 | 3/2008 |
| CN | 101146491 A | 3/2008 |
| CN | 101188982 | 5/2008 |
| CN | 101188982 A | 5/2008 |
| CN | 101252891 | 8/2008 |
| CN | 101878003 | 11/2010 |
| CN | 102202598 | 9/2011 |
| DE | 19959366 | 6/2001 |
| DE | 10340059 | 2/2005 |
| DE | 69636845 | 8/2007 |
| DE | 102006036020 | 2/2008 |
| DE | 102008054138 | 5/2010 |
| EP | 0015599 | 9/1980 |
| EP | 1062916 | 12/2000 |
| EP | 1547543 | 6/2005 |
| EP | 2039320 | 3/2009 |
| KR | 10-2007-0009060 | 1/2007 |
| WO | WO 97/43977 | 11/1997 |
| WO | WO 99/52466 | 10/1999 |
| WO | WO 02/26154 | 4/2002 |
| WO | WO 2004/008983 | 1/2004 |
| WO | WO 2004/073541 | 9/2004 |
| WO | WO 2004/080328 | 9/2004 |
| WO | WO 2006/109176 | 10/2006 |
| WO | WO 2008/011948 | 1/2008 |
| WO | WO 2010/049135 | 5/2010 |

OTHER PUBLICATIONS

Official Action with English Translation for China Patent Application No. 201280012017.8, dated Jun. 23, 2015, 12 pages.
International Search Report prepared by the European Patent Office on Jul. 31, 2007, for International Application No. PCT/EP2007/003480; Applicant, Holger Zipprich.
Written Opinion for International (PCT) Application No. PCT/EP2007/003480, mailed Apr. 20, 2007.
International Preliminary Report on Patentability prepared by the International Preliminary Examining Authority for International Application No. PCT/EP2007/003480 and English translation.
International Search Report prepared by the European Patent Office on Aug. 18, 2011 for International Application No. PCT/EP2011/002229.
International Search Report and Written Opinion prepared by the European Patent Office on Mar. 14, 2012, for International Application No. PCT/EP2011/005748.
International Search Report prepared by the European Patent Office on May 14, 2012, for International Application No. PCT/EP2012/000413.
Official Action for U.S. Appl. No. 12/297,570 mailed Apr. 11, 2011, 15 pages.
Official Action for U.S. Appl. No. 12/297,570 mailed Jan. 5, 2012, 9 pages.
Official Action for U.S. Appl. No. 12/297,570 mailed Jan. 3, 2013, 18 pages.

(56) References Cited

OTHER PUBLICATIONS

Official Action for U.S. Appl. No. 12/297,570 mailed May 31, 2013, 18 pages.
Official Action for U.S. Appl. No. 13/696,162 mailed Apr. 12, 2013, 15 pages.
Official Action for U.S. Appl. No. 13/696,162 mailed Feb. 24, 2014, 15 pages.
Official Action for U.S. Appl. No. 13/696,162 mailed Jul. 18, 2014, 20 pages.
Official Action for U.S. Appl. No. 13/696,162, mailed May 6, 2015 12 pages.
Official Action for U.S. Appl. No. 13/885,643, mailed Apr. 9, 2015 18 pages.
Official Action for U.S. Appl. No. 13/982,799, mailed Jul. 30, 2014, 11 pages.
Official Action for U.S. Appl. No. 13/982,799, mailed Mar. 3, 2015 7 pages.
Official Action for German Patent Application No. 102006018726.1, dated Jun. 24, 2015, 6 pages.
Official Action with English Translation for China Patent Application No. 201180062921.5, dated May 13, 2015, 13 pages.
Official Action with English Translation for China Patent Application No. 201280010689.5, dated Jul. 20, 2015, 11 pages.
Official Action for U.S. Appl. No. 12/297,570, mailed Mar. 22, 2016 15 pages.
Official Action for U.S. Appl. No. 13/696,162, mailed Nov. 20, 2015 13 pages.
Official Action for U.S. Appl. No. 13/696,162, mailed Jun. 3, 2016 14 pages.
Official Action for U.S. Appl. No. 13/885,643, mailed Dec. 17, 2015 24 pages.
Official Action for U.S. Appl. No. 13/982,799, mailed Oct. 8, 2015 8 pages.
Notice of Allowance for U.S. Appl. No. 13/982,799, mailed Mar. 15, 2016 6 pages.
Official Action for U.S. Appl. No. 12/297,570, mailed Oct. 26, 2016 14 pages.
Notice of Allowance for U.S. Appl. No. 13/696,162, mailed Sep. 2, 2016 5 pages.
Official Action for U.S. Appl. No. 13/885,643, mailed Aug. 11, 2016 31 pages.
Official Action with English Translation for China Patent Application No. 201280012017.8, dated Nov. 29, 2016, 12 pages.

* cited by examiner

FIG. 1
FIG. 2
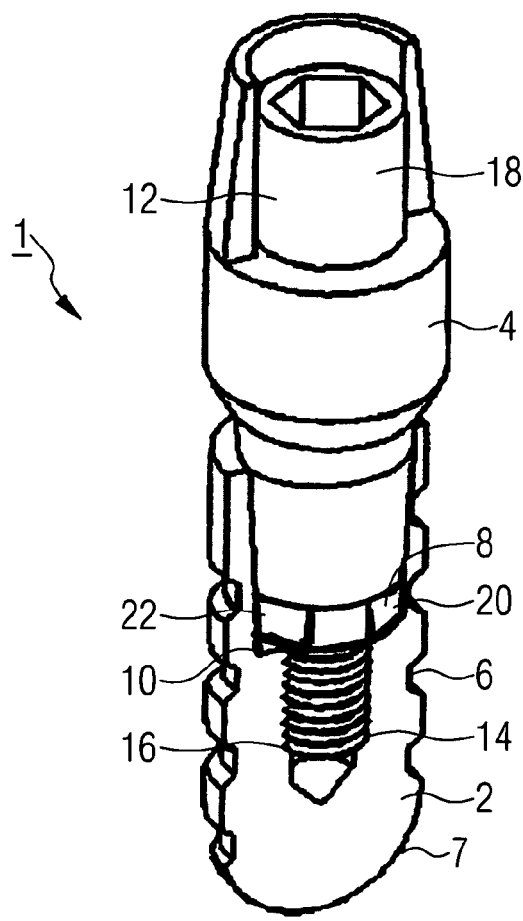
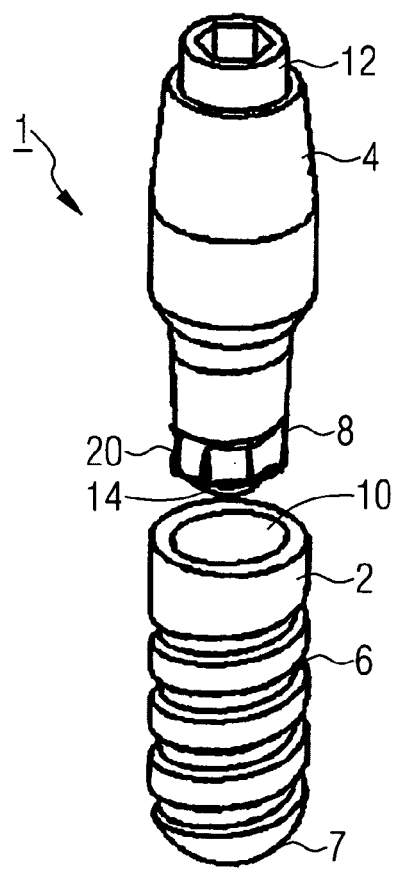

DENTAL IMPLANT SYSTEM

CROSS REFERENCE TO RELATED APPLICATIONS

This application is a national stage application under 35 U.S.C. 371 and claims the benefit of PCT Application No. PCT/EP2012/001220 having an international filing date of 20 Mar. 2012, which designated the United States, and which PCT application claimed the benefit of European Patent Application No. 11002296.9 filed on 21 Mar. 2011, the disclosures of which are incorporated herein by reference.

FIELD

The invention relates to a dental-implant system having a first implant part provided for being inserted into a jawbone and having a second implant part associated therewith, provided for fixing a dental prosthetic piece, the implant parts being mechanically connectable to each other via a connection pin which is formed onto one of the implant parts and which can be pushed into a receiving channel provided in the other implant part, and the outer cross-section of the connection pin and, matching said cross-section, the inner cross-section of the receiving channel associated therewith, are each designed in an indexing area as a polygon.

BACKGROUND OF THE INVENTION

Dental implants can be used in the reconstructive therapy to compensate for the loss of a tooth. They are usually inserted into the jawbone in the place of an extracted or shed tooth, in order to hold there, after a healing-in phase of approximately four to twelve weeks, a prosthetic part serving as a dental prosthesis or a crown. For this purpose, such a dental implant is usually configured as an appropriately shaped metallic body inserted into the jawbone by screwing-in, in the intended place. As a rule, the apical end of the dental implant includes a screw thread, in most cases a self-cutting screw thread, with which the dental implant is inserted into the correspondingly prepared implant bed.

To facilitate the insertion into the patient's mouth and in particular to enable a particularly extensive preparation of the prosthesis properly speaking for its being fixed on the implant already prior to the patient's treatment, for example in a dental laboratory, dental-implant systems can be of a multi-part configuration. In particular, a generally two-part construction can be provided, the dental-implant system comprising a first implant part, also referred to as the actual implant or post part, provided for being inserted into the jawbone, and in addition to this, a second implant part associated therewith, also referred to as mounting part, on which, in turn, the dental prosthetic piece provided as a prosthesis or the like can be mounted. The outer surface of the first implant part or post part is usually provided with a thread, which can be designed as a self-cutting thread or else as a not self-cutting thread. The post part is usually anchored in a correspondingly prepared implant bed of the jawbone. The construction of the thread provided in the external area of the dental implant is usually configured for a high primary stability of the arrangement and a uniform forwarding of the forces arising under the chewing load of the dental implant, into the jawbone.

Usually, a connection pin formed onto one of the implant parts, as a rule the mounting part, is provided for mechanically connecting the implant parts with each other. This pin can be pushed into a receiving channel provided in the other implant part, as a rule the post part. With regard to the choice of geometry and dimensioning, in particular of the cross-sections, the connection pin on the one hand and the receiving channel on the other hand are usually adapted to each other in such a way that mounting is relatively easy and, nevertheless, a good guidance of the components in each other and, thus, a sufficiently high mechanical stability can be achieved. The mounting part, whose upper part is usually fitted with a crown, another prothetic provision or the like in a manner known as such, can be glued together with the post part via the connection pin pushed into the receiving channel to ensure the mechanical connection. The mounting part can, however, also be pressed into the post part and fixed only via a clamping or else can additionally be fixed by cement or glue. It is, however, also usual to connect the mounting part and the post part with each other by means of a screw joint, wherein a suitable connection screw is passed through a corresponding channel in the mounting part and engages into an associated thread in the post part.

In view of the forces arising under the chewing load and the desired long service life when using such a dental implant, the mechanical stability of the arrangement under various loads is particularly important. In particular, as a rule, even a rotation or torsion between the mounting part and the post part through external forces, mostly due to the chewing load, shall be counteracted. For this purpose, usually a mechanical indexing in the form of a mechanical lock is used, or the surface pressure between the mounting part and the post part is suitably chosen. In particular, a suitable contouring of the cross-section of the connection pin on the one hand and the receiving channel associated therewith on the other hand can be provided for indexing and to avoid a rotation of the mounting part on the post part, to form the before-mentioned mechanical lock.

However, the mechanical lock between the mounting part and the post part of multi-part implant systems in the manner of an indexing does not only serve the purpose of counteracting a rotational load, but shall in particular also assist the correct insertion of the implant in the patient's mouth with high positional accuracy, keeping the treatment time as short as possible. After the insertion of the implant properly speaking, preferably after the post parts have healed in, the spatial and geometrical data of the remaining teeth (for example antagonist teeth, teeth located mesially and distally of the place of insertion), of the mucosa and of the post part or implant, or of the mounted mounting part have to be considered in such systems in order to manufacture the crown, the bridge or other prostheses. These spatial and geometrical data are needed to manufacture the crown, the bridge or the like with precise fitting and in an anatomically optimized manner.

The indexing, i.e. the determination of the possible rotational orientation between the mounting part on the one hand and the post part on the other hand is usually achieved by suitably specifying the contour of the cross-sections of the connection pin on the one hand and of the receiving channel on the other hand in the area of their connection. Usually, the outer cross-section of the connection pin and, matching said cross-section, the inner cross-section of the receiving channel associated therewith, are for that purpose each configured in a polygonal shape, in particular a hexagonal shape, in an indexing area which may extend over the entire length or else only over a section of the connection pin, viewed in longitudinal direction of the connection pin. Thus, a hexagonal connection allows six possibilities of positioning the mounting part on the post part when mounting the mounting part.

With such a configuration of the indexing area as a polygonal connection, the main design targets, namely a relatively simple mountability, on the one hand, and a relatively high accuracy of fit, on the other hand, shall be achieved. With regard to the mountability, it is in particular desired to find the correct mounting orientation easily and quickly and to avoid, at the same time, tiltings or the like, when inserting the connection pin into the receiving channel, so that the mounting part can be placed in the patient's mouth in a relatively short time and, thus, within a short treatment time. With regard to the accuracy of fit, however, it is desired to keep the rotational play between the components, i.e. between the connection pin on the one hand and the receiving channel in the post part, as small as possible in order to enable in this way a sufficiently high mechanical stability and a long service life of the implant system. However, these two design targets conflict with each other because a high accuracy of fit requires very tight tolerances of the components, so that the assembly requires a correspondingly accurate positioning of the components relative to each other, with increased danger of undesired tilting.

Therefore, the invention is based on the problem to provide a dental-implant system of the above-mentioned type which enables a particularly simple assembly in a relatively short mounting time, while keeping the accuracy of fit of the components high and the rotational play between the mounting part and the post part correspondingly small.

This task is solved according to the invention by the fact that the connection pin comprises in the indexing area at least two sections, the outer edges, viewed in the cross-section, being rounded more strongly in a first, end-side section than in a second section.

The invention starts out on the consideration that the simultaneous fulfillment of the two conflicting design targets can be achieved by creating on the connection pin individualized partial areas or sections, each of which is specifically configured for one of the design targets. In these partial areas or sections, the characteristic parameters shall suitably be chosen in view of the respective design target. In this connection, the rounding of the outer edges of the polygon is provided as the suitable parameter via which it is possible to differentiate between the above-mentioned design targets.

In fact, for reasons of production engineering, it is inevitable, when producing a polygon, that the edges are rounded to a certain extent contrary to the theoretical mathematical shape of a genuine acute angle. Depending on the requirement, the edges can be executed with high precision and in close approximation to a genuine acute angle, with relatively little rounding. An outer cross-section of the polygon designed in such a manner leads to a very high accuracy of fit when inserting the connection pin into the receiving channel associated therewith, and the rotational play is very small. However, in this case, a very precise alignment of the components to each other is necessary when joining them. By contrast, the edges of the polygon can also be executed with a relatively strong rounding. This allows certain tolerances regarding the alignment of the components to each other, but entails an increased rotational play between the components in the assembled system.

It is, therefore, possible to achieve the two before-mentioned design targets by combining preferably on the end-side at the indexing area of the connection pin a first section of the connection pin, specifically aiming at facilitating the assembly, with a second section of the connection pin, specifically aiming at minimizing the rotational play between the components. To facilitate the assembly and, in particular, the positioning of the components relative to each other, the first section has relatively strongly rounded outer edges and the second section, relatively slightly rounded outer edges.

Advantageous embodiments of the invention are the subject matter of the dependent claims.

In order to ensure a high mechanical stability of the system, the connection pin and in an accordingly matching manner, also the receiving channel in the other implant part are preferably designed with straight lateral faces extending substantially in parallel to the longitudinal axis of the connection pin. In order to make the assembly even easier, the connection pin is preferably designed such that in the end region of the indexing area, which is pushed into the receiving channel during assembly, its outer dimensions taper towards the free end. For this purpose, the rounded outer edges of the connection pin are advantageously designed in the first section with a conical taper towards the free end of the connection pin.

In order to particularly promote the mechanical stability of the system after mounting and to ensure in addition a certain tightness and, thus, a long service life, the connection pin includes in an advantageous development a further region which is specifically configured for that purpose. For that purpose, the connection pin is advantageously designed, in a sealing area, with a cross-section which tapers towards the free end of the connection pin, preferably in a conical manner.

In a particularly advantageous embodiment, the respective other implant part, which includes the receiving channel for the connection pin, i.e. in particular the so-called post part or implant properly speaking, is specifically designed for a particularly simple mounting, in particular for an assembly without tilting. In the manner of a construction adapted to the basic structure of the connection pin, the receiving channel advantageously includes for that purpose a channel end piece configured as a polygon socket and in front thereof, viewed in the direction of insertion of the connection pin, a channel piece whose cross-section tapers towards the channel end piece, namely, in another advantageous embodiment, in a conical manner.

In order to keep the assembly particularly simple and, furthermore, to avoid tiltings during assembly in a particularly effective manner, the channel piece has in a particularly advantageous embodiment, in the region immediately adjacent to the channel end piece, i.e. in the transition region to the channel end piece, a larger inner diameter than the inscribed circle of the polygon defined by the inner cross-section of the channel end piece. According to the conventional definition, the inscribed circle is that circle which touches each sideline of the cross-section of the polygon in one point only; that means that in case of an even-numbered symmetry of the polygon, the diameter of the inscribed circle is equal to the distance of two opposite sides from each other. As the end-side inner diameter of the channel piece is larger in comparison therewith, an abutment edge is formed in the transition region between the corners of the polygon lying thereunder, on which the connection pin of the respective other implant part can rest when the components are joined, if the rotational orientation is not completely correct.

In another advantageous embodiment, the inner diameter of the channel piece is, furthermore, in the region immediately adjacent to the channel end piece, smaller than the diameter of the circumscribed circle of the polygon defined by the inner cross-section of the channel end piece. According to the conventional definition, the circumscribed circle is that circle which passes through the corner points of the cross-section of the polygon; that means that in case of an even-numbered symmetry of the polygon, the diameter of the circumscribed circle is equal to the distance of two opposite corners from each other. As the end-side inner diameter of the channel piece is smaller in comparison therewith, the corner geometry of the polygon extends, in the transition region in the area of the corners of the polygon lying thereunder, from the channel end piece into the preferably conical transition region of the channel piece.

It is exactly by combining these geometry parameters with each other that the above-mentioned abutment edges are formed in the areas between the corners of the polygon, on which the end region of the connection pin can rest while the components are mounted, together with extensions of the corners of the polygon in the transition region. Due to the rounded end side of the outer contour of the connection pin, the latter can be rotated, while resting on the abutment edges, far enough to correct the rotational orientation without any significant risk of tilting, in a relatively unproblematic manner.

The abutment edge can be configured in a substantially level manner. In a further advantageous embodiment, however, the abutment edge formed in the contact area by the channel piece and the channel end piece is configured with a bevel. The angle of inclination of the abutment edge, in particular inwards towards the central axis of the receiving channel, is advantageously smaller than the triple, preferably smaller than the double, particularly preferably smaller than the 1.5 fold, of the cone angle in the sealing area. This ensures a reliable guidance of the connection pin during its insertion into the receiving channel.

The advantages achieved with the invention consist in particular in that the connection pin, which is configured in the indexing area with different geometry parameters in different sections, in particular with a rounding of the outer edges varying from one section to the other, makes it possible to achieve actually conflicting design targets for the overall system, namely a simple and fast mountability and, at the same time, a small rotational play. The rounding can be provided, as specified in the present case, for polygon-based systems. Of course, the rounding can also advantageously be applied in similar systems in which indexing is given by local maxima of the diameter.

BRIEF DESCRIPTION OF THE DRAWINGS

An exemplary embodiment of the invention is explained in detail by means of a drawing, in which:

FIG. 1 is a partly sectional view of a dental-implant system.

FIG. 2 is an exploded view of the dental-implant system of FIG. 1.

Identical parts are marked with the same reference numbers in all figures.

DETAILED DESCRIPTION

Figure 3:
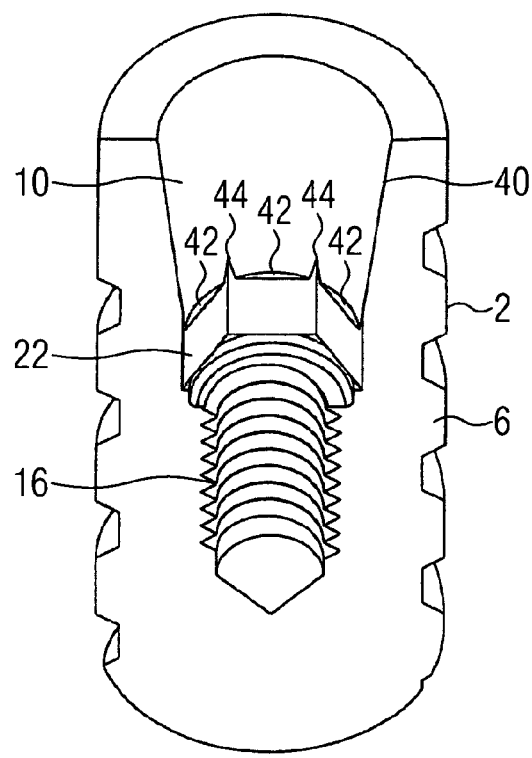
FIG. 3 is a partly sectional view of the post part of the dental-implant system of FIG. 1.
Figure 4:
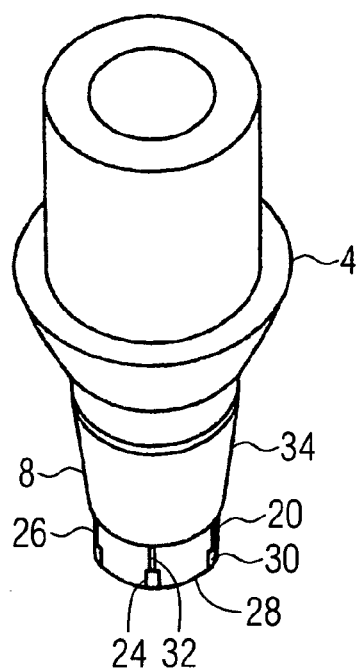
FIG. 4, 5 are an oblique and a lateral view of the mounting part of the dental-implant system of FIG. 1.
Figure 5:
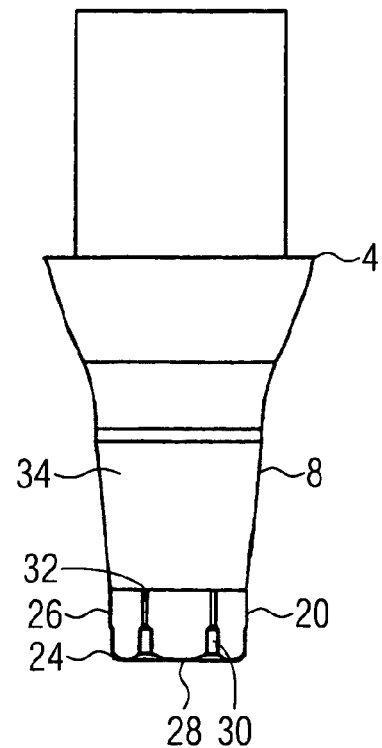

The dental implant 1 or dental-implant system shown in a partly sectional view in FIG. 1 in mounted state and in an exploded view in FIG. 2 is provided for use in the jawbone in the place of an extracted or shed tooth, in order to hold there a prosthetic part serving as a dental prosthesis or a crown. For this purpose, the dental implant 1 is of a multi-part configuration and comprises a first implant part 2 configured as a so-called post part and a second implant part 4 associated therewith, also referred to as mounting part, provided for fixing a dental prosthetic piece.

The first implant part 2 or post part is provided on its outside with an external thread 6, which is configured, in particular at its apical end 7, as a self-cutting screw thread, with which the first implant part 2 or post part can be inserted into the jawbone by screwing in, in the intended place. The pitch of the thread 6 can be uniform or else variable, it being possible to also take into consideration, through a suitable choice of parameters, any different biological conditions or the like, as well as different growing-in behaviors. Construction and configuration of the thread 6 are designed in particular in view of a desired high primary stability and a uniform forwarding of the forces arising under the chewing load of the dental implant 1, into the jawbone.

In order to enable an insertion into the post part or first implant part 2 with high mechanical stability, after having suitably fixed the dental prosthetic piece or the prosthesis on the mounting part or second implant part 4, a connection pin 8 is formed onto the second implant part 4, which can be pushed into a receiving channel 10 associated therewith, provided in the first implant part 2. By pushing the connection pin 8 into the receiving channel 10, the implant parts 2, 4 are mechanically connected with each other. The mechanical connection of the post part 2 and the mounting part 4 is effected via an associated connection screw 12, whose external thread 14 is screwed into an internal thread 16 provided in the post part 2, whereby the screw head 18 of the connection screw 12 presses the mounting part 4 onto the post part 2.

The dental implant 1 is specifically designed for ensuring, after a suitable preparation of the mounting part 4, a reliable and mechanically stable rotational orientation of the mounting part 4 even when relatively high forces arise, in particular through the chewing load. It should in particular also be possible to insert and integrate the mounting part 4 provided with the dental prosthetic piece into the post part 2 grown into the jawbone, in a relatively short treatment time. For this purpose, the outer contour of the connection pin 8 matches the inner contour of the receiving channel 10, it being possible that both of them are of conical shape, viewed in the longitudinal direction.

The outer contour of the connection pin 8—and the correspondingly adapted inner contour of the receiving channel 10—are as such configured in the exemplary embodiment with a cross-section having a multiple symmetry, so that a rotational locking mechanism is created when the above-mentioned components are joined and thus, a reliable rotational orientation of the mounting part 4 relative to the post part 2 can be set. For the purpose of such an indexing and for the formation of the before-mentioned rotational locking mechanism, the connection pin 8 comprises an indexing area 20 formed onto its end side, in which the outer cross-section of the connection pin is configured as a polygon in the exemplary embodiment, as a hexagon. In mounted state, the indexing area 20 engages into a corresponding associated channel end piece 22 located in the receiving channel 10. As can be seen in the sectional view of the post part or first implant part 2 of FIG. 3, the channel end piece 22 is configured with an inner cross-section matching the outer cross-section of the connection pin 8 in the indexing area 20, i.e. also as a hexagon socket.

The dental implant 1 is specifically designed for enabling a particularly simple mounting in a relatively short mounting time, while maintaining, nevertheless, a high accuracy of fit of the components, i.e. in particular of the connection pin 8 and the receiving channel 10, and a correspondingly small rotational play of the mounting part 4 relative to the post part 2. For this purpose, the connection pin 8 is of a multi-stage design in the indexing area 20, comprising two sections 24, 26, whose geometries and shapes are adapted to different design targets. In the first section 24, adjacent to the free end 28 of the connection pin 8, the contour of the indexing area 20 is such that a relatively simple and fast mounting and in particular an easier introduction of the indexing area 20 into the channel end piece 22 is ensured. For this purpose, the contour of the outer cross-section of the connection pin 8 is configured in the first section 24 for an error-tolerant positioning during joining of the implant parts 2, 4. This is achieved by a relatively strong rounding of the outer edges 30 of the polygon in the first section 24.

Figure 6:
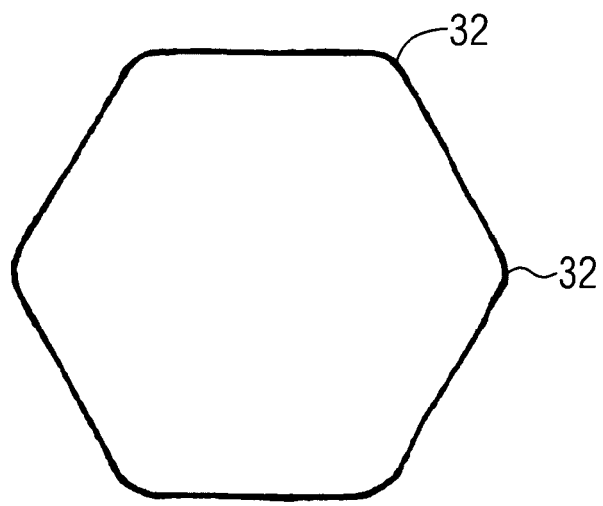
FIG. 6, 7 are cross-sectional views of the connection pin of the dental-implant system of FIG. 1.
Figure 7:
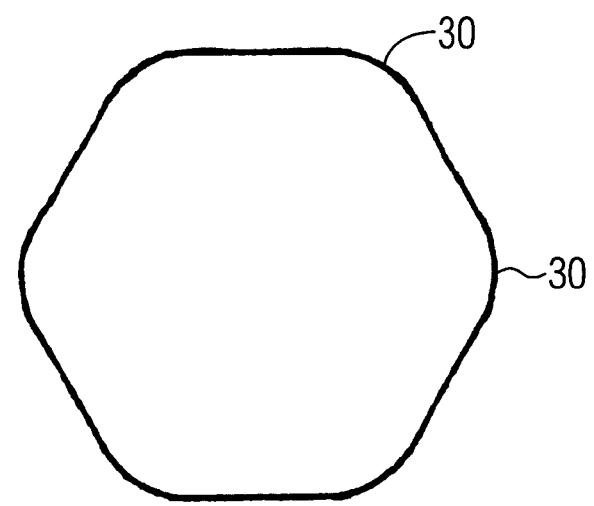

Contrary thereto, the second section 26 is specifically designed for minimizing the rotational play between mounting part and post part, by means of a suitable contour of the outer cross-section of the connection pin 8. For this purpose, the outer edges 32 of the polygon are only slightly rounded in the second section 26. By comparison, the dental implant 1 is configured such that the outer edges 30 of the polygon are rounded more strongly in the first, end-side section 24 of the connection pin 8 than the outer edges 32 in the second section 26 of the connection pin. This can be seen from the comparative representations of the cross-sections in FIG. 6, 7.

In order to make it even easier to mount and join the implant parts 2, 4, the rounded outer edges 30 of the connection pin 8 are designed in the first section 24 with a conical taper towards the free end 28 of the connection pin 8. Furthermore, the connection pin 8 is of a conical design in a sealing area 34, i.e. its cross-section tapers towards its free end 28.

As can be seen from the representation of the post part or first implant part 2 of FIG. 3, the post part or first implant part 2, too, is specifically designed, through a particularly suitable configuration of the receiving channel 10, for a particularly simple mounting, in particular for an assembly without tilting. In the manner of a construction adapted to the basic structure of the connection pin 8, the receiving channel 10 comprises for that purpose a channel piece 40 whose cross-section tapers towards the channel end piece, in the exemplary embodiment, in a conical manner, and which is located in front of the channel end piece 22 designed as a polygon socket, viewed in the direction of insertion of the connection pin 8.

The channel piece 40 has in its end area, which is immediately adjacent to the channel end piece 22, i.e. in the transition region to the channel end piece 22, a larger inner diameter than the inscribed circle of the polygon defined by the inner cross-section of the channel end piece 22. As the end-side inner diameter of the channel piece 40 is larger in comparison therewith, abutment edges 42 are formed between each two corners of the polygon in the transition region, on which the connection pin 8 can rest when the components are joined, if the rotational orientation is not completely correct.

The free end 28 of the connection pin 8 can temporarily rest on the abutment edges 42, if the rotational orientation is at first still relatively inaccurate. After a subsequent correction of the rotational orientation, the connection pin 8 will slide into the channel end piece 22, at first with its first section 24, which is adjacent to the free end 28. Upon the transition from the first section 24 to the second section 26, which implies steps in the area of the outer edges 30, 32, due to the latter's different roundings, these steps will also hit the abutment edges 42 if the rotational orientation is not yet completely correct. This gives the operator the possibility to perfect the rotational orientation through a readjustment, so that the second section 26 can also be pushed into the channel end piece 22. It is, thus, exactly by means of the cooperation of the abutment edges 42 with the steps created through the different roundings of the outer edges 30, 32 that a highly precise orientation is achieved with, at the same time, a particularly simple insertability and, therefore, a great assembly-friendliness.

Furthermore, the inner diameter of the channel piece 40 is in the region immediately adjacent to the channel end piece 22 smaller than the diameter of the circumscribed circle of the polygon defined by the inner cross-section of the channel end piece 22. As the end-side inner diameter of the channel piece 40 is smaller in comparison therewith, extensions 44 of the corner geometry of the polygon are formed in the area of the corners of the polygon lying thereunder, in the transition region from the channel end piece 22 into the conically shaped transition area of the channel piece 40.

Furthermore, the abutment edge 42 formed by the channel piece 40 and the channel end piece 22 in the area of contact is beveled. The angle of inclination of the abutment edge 42, in particular inwards towards the central axis of the receiving channel 10, is in the exemplary embodiment smaller than the 1.5 fold of the cone angle in the sealing area 34. This ensures in a particularly favorable manner a reliable guidance of the connection pin 8 during its insertion into the receiving channel 10.

In an advantageous embodiment, the screw-joint system, too, is suitably designed for a particularly high mounting safety. This can be achieved in particular by choosing a suitable length of the connection screw 12 in view of the dimensions of the mounting part 4 and the position of the internal thread 16 in the post part 2. Preferably, the length of the connection screw 12 is chosen such that its external thread 14 does not yet engage into the internal thread 16 in case of an incorrect rotational orientation in which the free end 28 of the connection pin 8 still rests on the abutment edges and, therefore, does not yet protrude into the channel end piece 22. With such a particularly preferred choice of the screw length, a screwing together of the implant parts by tightening the connection screw 12 is, therefore, only possible when the rotational orientation of the implant parts relative to each other is correct, so that the connection pin 8 can be pushed into the channel end piece 22 in the indexing area 20 and thus, the external thread 14 can engage into the internal thread 16.

LIST OF REFERENCE NUMBERS

1 Dental implant
2 Implant part
4 Implant part
6 External thread
7 Apical end
8 Connection pin
10 Receiving channel
12 Connection screw
14 External thread
16 Internal thread 18 Screw head
20 Indexing area
22 Channel end piece
24, 26 Section
28 Free end
30, 32 Outer edge
34 Sealing area
40 Channel piece
42 Abutment edge
44 Extension

The invention claimed is:

1. A dental implant, comprising:
a first implant part provided for being inserted into a jawbone;
a second implant part associated therewith, provided for fixing a dental prosthetic piece;
a connection pin for mechanically connecting the first and second implant parts to each other, the connection pin has a longitudinal axis and is formed onto the second implant part, and the connection pin is configured to push into a receiving channel provided in the first implant part;
wherein an outer cross-section of the connection pin matches an inner cross-section of the receiving channel;
wherein the connection pin comprises an indexing area having a first section disposed proximate to an end of the connection pin and a second section disposed adjacent to said first section, wherein the outer cross-section of the connection pin in the first section is constant along the longitudinal axis of the connection pin, and wherein the outer cross-section of the connection pin in the second section is constant along the longitudinal axis of the connection pin; and
wherein the outer cross-section of the connection pin in the first section is polygon-shaped with flat sides and radiused edges, and the outer cross-section of the connection pin in the second section is polygon-shaped with flat sides and radiused edges, and wherein a radius of curvature of the first section's radiused edges is larger than a radius of curvature of the second section's radiused edges.

2. The dental implant of claim 1, wherein the connection pin has, in a sealing area, a cross-section tapering towards the end of the connection pin, and the sealing area has a conical configuration.

3. The dental implant of claim 1, wherein the receiving channel comprises a channel end piece configured as a polygon socket, and a channel piece whose inner cross-section tapers towards the channel end piece at a cone angle that matches a sealing area of the connection pin, and said channel end piece is arranged in front of said channel piece when viewed in the direction of insertion of the connection pin.

4. The dental implant of claim 3, wherein the inner cross-section of the channel piece is conical.

5. The dental implant of claim 3, wherein the inner cross-section of the channel piece in a region immediately adjacent to the channel end piece is larger than an inscribed circle of the polygon defined by the inner cross-section of the channel end piece.

6. The dental implant of claim 5, wherein an abutment edge formed by the channel piece and the channel end piece in an area of contact of said channel piece and the channel end piece is beveled, wherein the beveled abutment edge comprises an angle of inclination.

7. The dental implant of claim 6, wherein the angle of inclination comprises an upper limit in size, and wherein the upper limit is no more than three times the cone angle in the sealing area.

8. The dental implant of claim 7, wherein the upper limit is two times the cone angle in the sealing area.

9. The dental implant of claim 8, wherein the upper limit is 1.5 times the cone angle in the sealing area.

10. The dental implant of claim 3, wherein the inner cross-section of the channel piece in a region immediately adjacent to the channel end piece is smaller than a diameter of a circumscribed circle of the polygon defined by the inner cross-section of the channel end piece.

11. A dental-implant, comprising:
a first implant part provided for being inserted into a jawbone;
a second implant part associated therewith, provided for fixing a dental prosthetic piece;
a connection pin for mechanically connecting the first and second implant parts to each other, the connection pin formed onto the second implant part, and the connection pin is configured to push into a receiving channel provided in the first implant part, wherein an outer cross-section of the connection pin matches an inner cross-section of the receiving channel;
wherein the connection pin comprises an indexing area having a first section disposed proximate to an end of the connection pin and a second section disposed adjacent to said first section, and
wherein the outer cross-section of the connection pin in the first section is polygon-shaped with flat sides and radiused edges, and the outer cross-section of the connection pin in the second section is polygon-shaped with flat sides and radiused edges, and wherein a radius of curvature of the first section's radiused edges is larger than a radius of curvature of the second section's radiused edges;
wherein the outer cross-section of the connection pin in the first section is constant along a longitudinal axis of the connection pin, and wherein the outer cross-section of the connection pin in the second section is constant along the longitudinal axis of the connection pin;
a channel end piece of the receiving channel configured as a polygon socket;
a channel piece whose inner cross-section tapers towards the channel end piece at a cone angle that matches a sealing area of the connection pin, and said channel end piece is arranged in front of said channel piece when viewed in the direction of insertion of the connection pin;
an abutment edge formed between the channel piece and the channel end piece wherein the abutment edge is bevelled and comprises an angle of inclination.

12. The dental implant of claim 11, wherein the inner cross-section of the channel piece is conical.

13. The dental implant of claim 11, wherein the angle of inclination comprises an upper limit in size, and wherein the upper limit is no more than three times the cone angle in the sealing area.

14. The dental implant of claim 13, wherein the inner cross-section of the channel piece in a region immediately adjacent to the channel end piece is smaller than a diameter of a circumscribed circle of the polygon defined by the inner cross-section of the channel end piece.

15. The dental implant of claim 14, wherein the upper limit is 1.5 times the cone angle in the sealing area.

16. The dental implant of claim 11, wherein the inner cross-section of the channel piece in a region immediately adjacent to the channel end piece is smaller than a diameter of a circumscribed circle of the polygon defined by the inner cross-section of the channel end piece.

\* \* \* \* \*